US00PP17347P2

(12) United States Plant Patent
Radler

(10) Patent No.: US PP17,347 P2
(45) Date of Patent: Jan. 9, 2007

(54) CLIMBING ROSE PLANT NAMED 'WEKRADLER'

(50) Latin Name: *Rosa hybrida*
Varietal Denomination: WEKradler

(75) Inventor: William J. Radler, Greenfield, WI (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 11/252,502

(22) Filed: Oct. 17, 2005

(51) Int. Cl.
*A01H 5/00* (2006.01)

(52) U.S. Cl. ..... Plt./111

(58) Field of Classification Search ..... Plt./111
See application file for complete search history.

*Primary Examiner*—Kent Bell
*Assistant Examiner*—June Hwu
(74) *Attorney, Agent, or Firm*—Christine, Parker & Hale, LLP

(57) ABSTRACT

A new variety of Climbing Rose suitable for garden decoration, having flowers of lemon yellow coloration.

1 Drawing Sheet

Classification: The present invention relates to a new *Rosa hybrida* plant.

Variety denomination: The new plant has the varietal denomination 'WEKradler'.

BACKGROUND OF THE INVENTION

This invention relates to a new and distinct variety of Climbing Rose. It was discovered in the summer of 1998 in Greenfield, Wis. as a mutation naturally occurring sport of the cultivar Autumn Sunset (not patented).

SUMMARY OF THE INVENTION

Among the features which distinguish the new variety from other presently available and commercial rose cultivars known to the inventor are the following combination of characteristics: its numerous red styles, its numerous stipitate glands on the peduncle that bear a fragrance of sweet juniper, its lemon yellow flowers with moderate fruity to spicy fragrance and its stipitate glands on numerous locations (on the stipules margins, on the tips of the new shoots, on the surface of the bud and on the lower portion of the receptacle). The plant has a spreading climbing growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKradler' may be asexually propagated by cuttings, budding and grafting. The budding and grafting successfully occurred on the plant/rootstock *Rosa hybrida* 'Dr. Huey'.

Comparison with parents

The new rose may be distinguished from its parent, Autumn Sunset by the following combination of characteristics: whereas 'WEKradler' bears flowers of lemon yellow coloration, the parent bears flowers of warm apricot gold coloration.

Comparison with the closest commercially available cultivar

The closest commercially available cultivar to the new variety is the parent Autumn Sunset.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety usually bears its flowers in clusters of three to six or more per stem. Flowers are borne in moderately regular rounded clusters on strong short to long stems (about 25 to about 128 cm). Outdoors, the plant blooms abundantly and nearly continuously during the growing season. The flowers have a moderate fruity to spicy fragrance.

BUD

The peduncle is about 2.5 to about 5.0 cm in length, of average caliper (about 0.2 to about 0.3 cm in diameter) and usually erect but sometimes bending. It is moderately rough, with numerous stipitate glands and few very small prickles. The stipitate glands bear a fragrance of sweet juniper. Peduncle color is between 144B and 146B, sometimes lightly suffused, especially on the side exposed to the sun, with between 187B and 183A.

Before the calyx breaks, the bud is about 1.0 to about 1.8 cm in diameter at the widest point, about 1.2 to about 2.4 cm in length, and pointed to moderately ovoid in shape. The surface of the bears very few foliaceous appendanges and many stipitate glands, usually with slender foliaceous parts extending beyond the tip of the bud about ¼ or more of its length. The stipitate glands occur on surface of sepals and on the sepals' margin. Bud color is between 146B and 137C sometimes lightly suffused, especially on the side exposed to the sun, with between 187B and 183A.

The sepals are about 2.1 to about 3.1 cm in length and about 0.6 to about 1.1 cm in width at the widest point. The outer surface color of the sepal is between 146B and 137C sometimes lightly suffused, especially on the side exposed to the sun, with between 187B and 183A. The inner surface color of the sepal is between 137C and 138B and covered with fine wooly tomentum; sepal margins are lined with numerous stipitate glands and few hairs.

The receptacle of the flower is of medium length (about 0.6 to about 0.9 cm) and somewhat heavy in caliper (about 0.7 to about 0.9 cm in diameter). The receptacle is globular to almost rounded in form. Its surface is somewhat smooth with some hairs and stipitate glands at the lower portion near the peduncle. It has thick fleshy walls. The receptacle color is between 144A and 137C.

As the petals open (after the calyx breaks), the bud is about 2.0 to about 2.7 cm in diameter at the widest point, about 2.7 to about 3.4 cm in length, and ovoid to somewhat globular in form. The color of the under and upper surfaces of the newly opened petals is between 12A and 14C sometimes lightly blushed with between 31B and 34C. There is no visible change in coloration at the point where the petal attaches.

BLOOM

When fully open, the bloom ranges from about 9.0 to about 13.1 cm in diameter. Petalage is double with about 18 to 27 petals and about 3 to 14 petaloids irregularly arranged. When partially open, the bloom form is moderately cupped and the petals are loosely spiraled to cupped with petal edges somewhat reflexed outward. When fully open, the bloom form is irregular to cupped and the petals are inversely cupped with petal edges moderately reflexed outward.

PETALS

The substance of the petals is moderately slight and of thin thickness, with upper surfaces moderately satiny and under surfaces slightly shiny. The petals are about 3.7 to about 5.1 cm in length and about 2.9 to about 5.4 cm in width at the widest point. Petal margins are entire.

The outer petals are nearly rounded to somewhat obovate in shape with rounded apices.

The inner petals are moderately obovate in shape with rounded apices.

Petaloids are about 1.5 to about 3.9 cm in length and about 0.6 to about 3.1 cm in width at the widest point. Petaloids are irregularly shaped somewhat oblanceolate to oblong with rounded apices.

NEWLY OPENED FLOWER

The under surface color of the outer petals is between 2D and 4D. There is no visible change in coloration at the point where the petal attaches on the under surface. On the upper surfaces of the outer petals, the color at the base of the petals is between 7D and 10A, gradually suffusing toward the edge of the petals with between 2D and 4D.

The under surface color of the intermediate and inner petals is between 10A and 10B. These is no visible change in coloration at the point where the petal attaches on the under surface. On the upper surfaces of the intermediate and inner petals, the color at the base of the petals is between 12A and 15C, gradually suffusing toward the edge of the petals with between 10A and 10B.

The under and upper surface color of the petaloids are similar in coloration to the upper and under surfaces of the intermediate and inner petals.

The general tonality of the newly opened flower is between 12A and 15C that gradually suffuses toward the edge of the petals with between 10A and 10B.

THREE-DAY-OLD FLOWER

The under surface color of the outer, intermediate and inner petals is between 2D and 4D. There is no visible change in coloration at the point where the petal attaches on the under surface. On the upper surfaces of the outer, intermediate and inner petals, the color at the base of the petals is between 7D and 10B, gradually suffusing toward the edge of the petals with between 2D and 4D.

The under and upper surface color of the petaloids are similar in coloration to the upper and under surfaces of the intermediate and inner petals.

The general tonality of the three-day-old flower is between 7D and 10B that gradually suffuses toward the edge of the petals with between 2D and 4D.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 55) and are arranged regularly about the pistils; some are mixed with petaloids. The filaments are of medium to long length (about 0.7 to about 1.5 cm) most with anthers. Filaments are between 13A and 14B in color. The anthers are about 0.2 to about 0.4 cm in length and about 0.1 to about 0.2 cm at their widest point and all open approximately at the same time. Anther color is between 21B and 8C when immature and between 200C and 163B at maturity. Pollen is moderately abundant and between 15B and 16A in color.

FEMALE REPRODUCTIVE ORGANS

Pistils vary in number (average about 100). The styles are moderately even, somewhat long in length (about 0.5 to about 0.9 cm), average in caliper and loosely bunched. Stigma color is between 20B and 21D. Style color is between 1D and 154D usually heavily suffused with near 53A. Ovaries are usually all enclosed in the calyx.

Hips are of average length (about 1.4 to about 2.0 cm), very rounded in form, and between 15B and 17C in color when ripe. The hip surface is mostly smooth sometimes with stipitate glands in the lower portion near the peduncle and with thick fleshy walls. The sepals are moderately permanent and usually straight in shape.

The seeds are irregularly rounded, smooth in texture, approximately 3 to about 8 per hip, about 0.4 to about 0.6 cm in diameter at the widest point and between 164D and 165D in color.

FOLIAGE

The compound leaves are usually comprised of three to seven leaflets and are borne abundantly. The seven-leaflet leaves are about 8.7 to about 13.4 cm in length and about 6.0 to about 11.5 cm in width at the widest point, moderately crisp to somewhat leathery in texture and semi-glossy in finish. The terminal leaflets are about 3.7 to about 6.6 cm in length and about 2.1 to about 3.4 cm in width at the widest point, shaped oval with acute apices and rounded to moderately acute bases. Their margins are usually simply serrate.

The upper surface color of the mature leaf is between 147A and 139A. The under surface color of the mature leaf is between 147B and 138B. The upper surface color of the young leaf is between 146A and 137C, usually heavily suffused with between 183A and 187B. The under surface color of the young leaf is between 146B and 138B, usually heavily suffused with between 183A and 187B.

The rachis is moderately light in caliper. The upper side is shallowly grooved with some hairs and stipitate glands on the edges of the grooves. The under side of the rachis is usually smooth but sometimes irregularly rough with no hairs or stipitate glands but sometimes with very few small prickles. The rachis color is between 146A and 144A sometime moderately suffused, especially on the new shoots with between 183A and 187B.

The stipules are about 1.1 to about 1.7 cm in length and of moderately narrow width (about 0.3 to about 0.5 cm) with medium length straight points that usually turn out at an angle of more than 45 degrees and often recurve toward the stem. Stipules margins are lined with numerous stipitate glands. The stipules color is between 144A and 146B sometime moderately suffused, especially on the new shoots with between 183A and 187B.

The petiole is moderately light in caliper. The upper side is shallowly grooved with some hairs and stipitate glands on the edges of the grooves. The under side of the petiole is usually smooth but sometimes irregularly rough with no hairs or stipitate glands but sometimes with very few small prickles. The petiole is about 0.5 to about 1.0 cm in length and about 0.1 to about 0.15 cm in diameter at the widest point. The petiole color is between 146A and 144A sometime moderately suffused, especially on the new shoots with between 183A and 187B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a spreading climbing growing habit with canes about 250 to about 380 cm in length with full branching. It displays very vigorous growth and the canes are of medium caliper for the class.

The color of the major stems is between 146B and 152B. They bear some large prickles that are about 0.7 to about 1.1 cm in length. The large prickles are slightly angled downward with a somewhat short length narrow oval base; prickle color is between 199C and 201B. The major stem bears no small prickles.

The color of the branches is between 146B and 137B sometimes lightly suffused with between 187B and 183B. They bear some large prickles which are of similar size and shape to the large prickles on the major stems; prickle color is between 146D and 160C.

The color of the new shoots is between 144A and 146B often lightly suffused with between 187B and 183B. They bear some large prickles which are of similar size and shape to the large prickles on the major stems; prickle color is between 146D and 145B usually moderately suffused with near 183D. The shoots bear no small prickles. The tips of the new shoots bear numerous stipitate glands.

I claim:

1. A new and distinct Climbing rose plant of the variety substantially as described and illustrated herein.

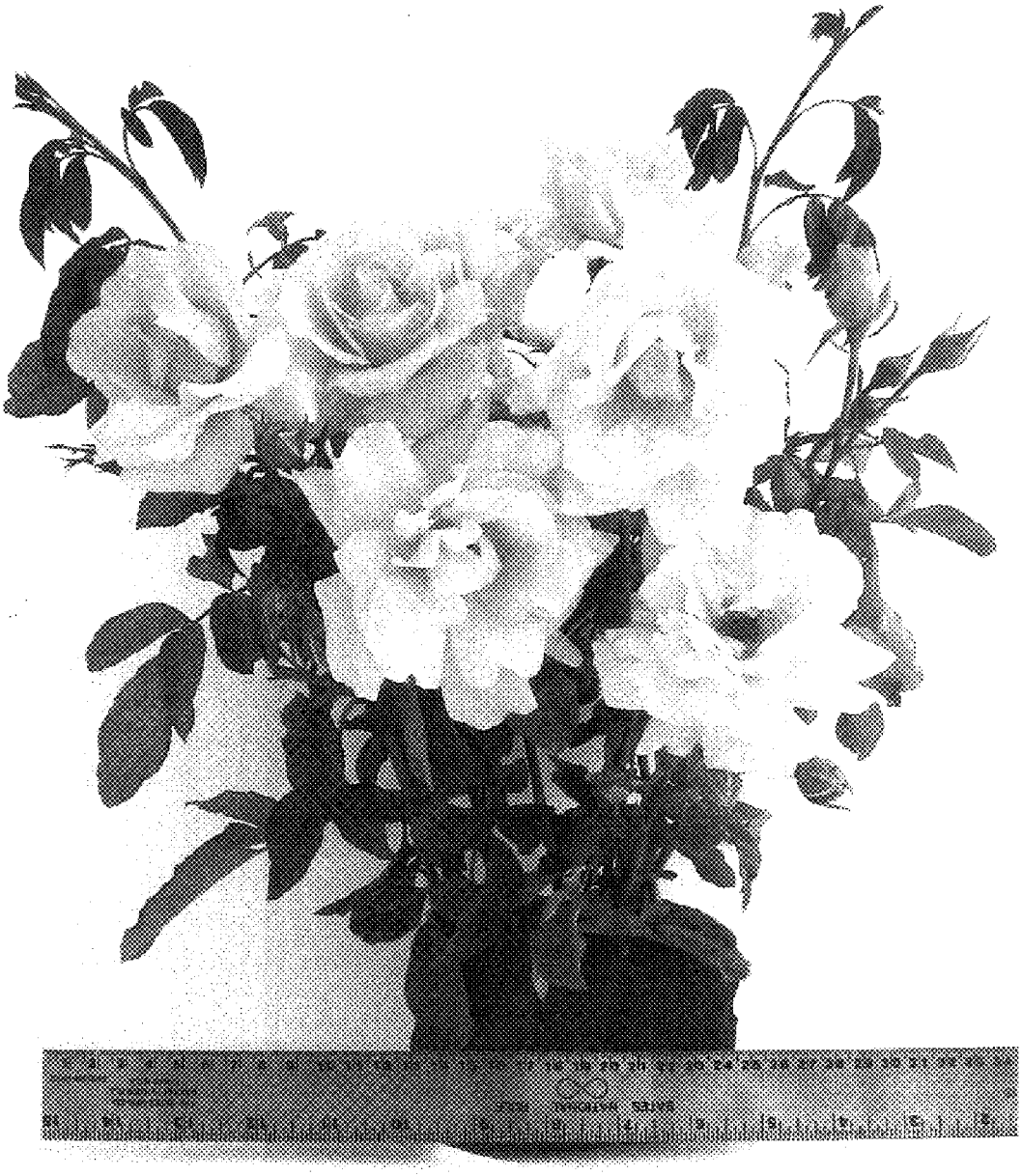

* * * * *